United States Patent [19]

Matteson et al.

[11] Patent Number: 5,681,978
[45] Date of Patent: Oct. 28, 1997

[54] METHOD FOR THE STEREOCONTROLLED SYNTHESIS OF STEGOBINONE AND USEFUL BORANE INTERMEDIATES

[75] Inventors: Donald S. Matteson, Moscow, Id.; Hon-Wah Man, Newark, Del.; Oliver Ho, Arlington, Mass.

[73] Assignee: Washington State University Research Foundation, Pullman, Wash.

[21] Appl. No.: 510,352

[22] Filed: Aug. 2, 1995

Related U.S. Application Data

[63] Continuation-in-part of Ser. No. 88,827, Jul. 7, 1993, abandoned.
[51] Int. Cl.$^6$ .................................................. C07F 5/02
[52] U.S. Cl. .................................................. 558/288; 549/416
[58] Field of Search .............................. 549/416; 558/288

[56] References Cited

PUBLICATIONS

Brown, H.C., and Garg, C.P., (1961) "The Chromic Acid Oxidation of Organo–boranes—A Convienient Procedure for Converting Olefins into Ketones via Hydroboration," *J. Am. Chem. Soc.* 83:2951–2.

Griffith, W.P., et al. (1987) "Preparation and use of Tetra–n–butylammonium Per–ruthenate (TBAP reagent) and Tetr–n–-propylammonium Per–ruthenate (TPAP reagent) as New Catalytic Oxidants for Alcohols," *J. Chem. Soc., Chem. Commun.* 21:1625–7.

Kodama, H., et al., (1987) "Stegobiol, A New Sex Phermone Component of Drugstore Beetle (*Segobium paniceum* L.)," *J. Chem. Ecol.* 13:1871–1879.

Kuwahara, Y., et al., (1978) "Chemical Studies on the Anobiidae: Sex Pheromone of the Drugstore Beetle, *Stegobium paniceum* (L.) (Coleoptera)," *Tetrahedron* 34:1769–1774.

Matteson, D.S., and Man, H.–W., "High–Precision Asymmetric Synthesis of Stegobiol of Stegobinone via Bornic Esters," (1993) *J. Org. Chem.* 58:6545–6547.

Matteson, D.S., et al., (1990) "Synthesis of Assymetrically Deuterated Glycerol and Dibenzylglyceraldehyde via Boronic Esters," *J. Am. Chem. Soc.* 112:3964–3969.

Ware, J.C., and Taylor, T.G., (1963) "Electrophilic Substitution. Chromic Acid Cleavage of Carbon–Boron Bonds," *J. Am. Chem. Soc.* 85:3026–7.

White, P.R., and Birch, M.C., (1987) "Female Sex Phermone of the Common Furniture Beetle Anobium punctatum (Coleoptera: Anobiidae): Extraction, Identification and Bioassays," *Chem. Ecol.* 13:1695–1706.

*Primary Examiner*—Nicky Chan
*Attorney, Agent, or Firm*—Fish & Richardson P.C.

[57] ABSTRACT

A method of synthesis of (2S,3R,1'R)-stegobinone(I) using borane intermediates and methods for the use of stegobinone (I) for attracting beetles of the Anobium species.

14 Claims, No Drawings

5,681,978

1

METHOD FOR THE STEREOCONTROLLED SYNTHESIS OF STEGOBINONE AND USEFUL BORANE INTERMEDIATES

STATEMENT AS TO RELATED APPLICATIONS

This application is a continuation-in-part of U.S. patent application Ser. No. 08/088,827, filed Jul. 7, 1993, now abandoned herein specifically incorporated by reference and to which is claimed priority under 35 USC §120.

STATEMENT AS TO FEDERALLY SPONSORED RESEARCH

This invention was supported in part by National Science Foundation grant CHE-8922672. The U.S. Government may have rights in this invention.

FIELD OF THE INVENTION

This invention relates to a method for the stereocontrolled asymmetric synthesis of (2S, 3R, 1'R)-stegobinone (I), which is the attractant pheromone of certain pest species of beetles of the family Anobiidae. Borane intermediates used in this method provide improved efficiency in the synthesis of (I) in high purity.

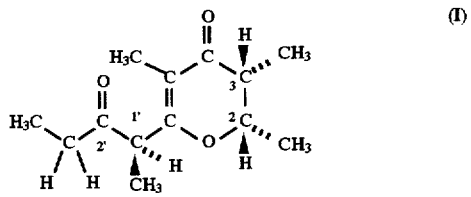

(I)

BACKGROUND OF THE INVENTION

This invention relates to a new and useful process for the synthesis of (2S, 3R, 1'R)-stegobinone (I), hereinafter referred to as "stegobinone". Stegobinone (I) is the active component of the pheromone of the drugstore beetle (*Stegobium paniceum*), a pest of stored grain. (Kuwahara et al. (1978) Tetrahedron 34:1769-1774). Stegobinone (I) is also the pheromone of the furniture beetle, *Anobium punctatum*, a wood eating pest species. (White & Birch (1987) Chem. Ecol. 13:1695-1706). This structure is illustrated above and is illustrated immediately following in the conventional abbreviated style which is used hereinafter. A second compound known as stegobiol (II) is used as the immediate precursor of stegobinone (I), a minor natural component of the drugstore beetle pheromone (Kodama et al. (1987) J. Chem. Ecol. 13:1871-1879).

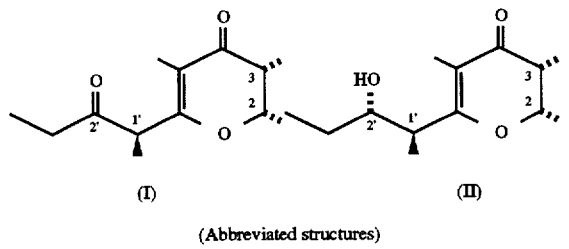

(I)        (II)

(Abbreviated structures)

More particularly, the invention relates to an improved synthetic route to stegobinone (I) via stegobiol (II) which utilizes several novel boronic ester intermediates. An earlier route of synthesis is described in copending application U.S. Ser. No. 08/088,827, and in a publication (Matteson & Man

2

(1993) J. Org. Chem. 58:6545-6547). According to the earlier synthesis, a sequence of highly stereoselective Lewis acid catalyzed homologations of boronic esters with (dihalomethyl)lithium leads to a single intermediate (III) that contains all of the necessary chirality to serve as a precursor to two intermediates that can be combined in a convergent manner to provide the entire carbon skeleton of stegobiol (II), which is converted to the active pheromone stegobinone (I). The novel intermediates described herein require fewer steps to prepare and provide a higher yield of stegobinone (I) than the previously described route.

SUMMARY OF THE INVENTION

The present invention provides an alternate, more efficient route to stegobiol (II).

The first stage of the new process involves construction of a keto boronic ester (X) from (III) via a series of transformations outlined in general form in the flow chart, the most significant innovation being in the hydrolytic conversion of hydroxy boronic ester (V) to the 1,2-oxaborolane (VII). An important feature of this step is the efficient recovery of the chiral diol (VI) used to direct the construction of the asymmetric centers in (IV) and other intermediates. The 1,2-oxaborolane (VII) is converted to a boronic ester (IX) with a relatively inexpensive and oxidation resistant diol before oxidation of the alcohol function to ketone (X).

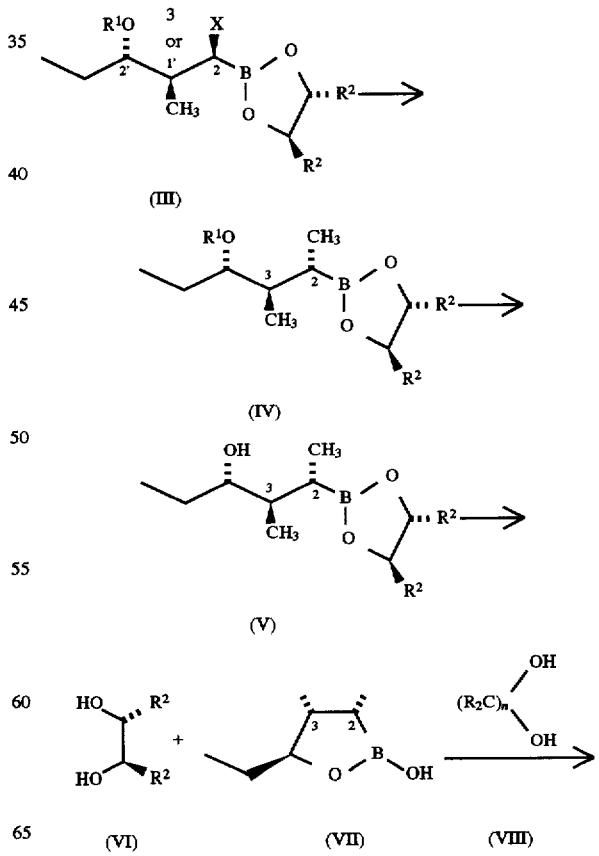

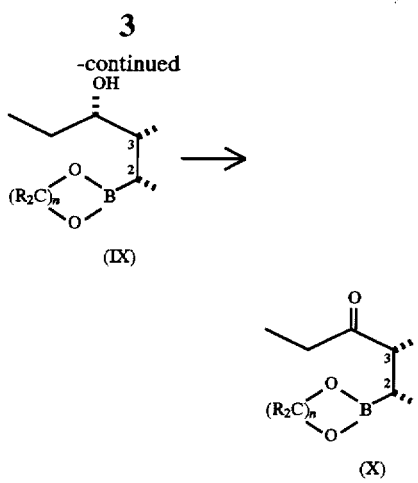

The second stage of the new process involves the conversion of the intermediate ketone (X) to a boron enolate (XII) by the use of a dialkylboron halide (XI), followed by aldol condensation of (XII) with the previously described aldehyde (XIII) to form an intermediate (XIV) containing all of the asymmetric centers of stegobiol (II). Conversion of intermediate (XIV) to O-protected stegobiol (XV) via oxidation and acid catalyzed ring closure concludes the new route. A conversion of an example of (XV) to stegobiol (II) has been described previously (Matteson & Man (1993) supra).

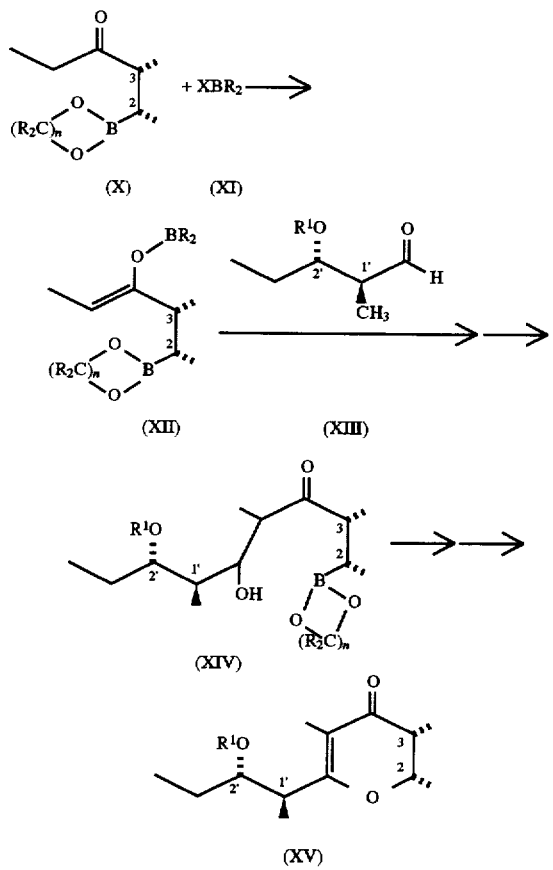

The invention also provides a method of attracting beetles of the Anobiid species by providing a sufficient amount of stegobinone (I) in a trap to attract the beetles. The method of the invention can be used to kill Anobiid beetles by providing a combination of stegobinone (I) to attract the beetles, and a toxic substance to kill the attracted beetles.

Other aspects of the invention will become apparent from the following detailed description and the claims.

DESCRIPTION OF THE INVENTION

As in an earlier described synthesis of stegobiol (Matteson & Man (1993) J. Org. Chem. 58:6545–6547), the key intermediate described by structure (III) is used as the source of two intermediates that can be continued subsequently in an aldol condensation to provide the entire carbon skeleton, including all of the asymmetric centers, of stegobiol (II). One particular example of (III) is (4R,5R, 1'S,2'S, 3'S)-2-(3'-benzyloxy-1'-chloro-2'-methylpentyl)-4,5-dicyclohexyl-1,3,2-dioxaborolane (III, $R^1$=benzyl, X=Cl, $R^2$=cyclohexyl). On this and the other intermediates illustrated, the numbers by the chiral carbons indicate to which of the chiral carbon(s) of stegobiol (II) each transforms and not to the name of the intermediate itself.

The novel route to stegobiol involves the preparation of a keto boronic ester (X), which is combined with the aldehyde (XIII) in an aldol condensation to form the carbon skeleton of stegobiol (II). The previously described synthesis utilizes an aldol condensation of a protected hydroxy ketone with the aldehyde (XIII), which has a simple derivative of a hydroxyl group, for example a silyloxy group, in place of the boronic ester group of keto boronic ester (X). The present invention reduces the number of protection and deprotection steps required by keeping the boron-carbon bond intact until a very late stage of the synthesis.

Intermediate boronic ester (IV) is derived from (III) as previously described (Matteson & Man (1993) supra). The group $R^1$ may be any hydroxy-protecting group which survives the conditions of the synthesis of (IV) and then can be cleaved by catalytic hydrogenation or other means to provide the hydroxyl group of (VI). The preferred $R^1$ group is benzyl. The group $R^2$ may be any alkyl group of sufficient size and geometry to provide asymmetric direction to reactions performed at nearby sites. Preferred group for $R^2$ is the cyclohexyl group, though other alkyl groups such as isopropyl are also known to provide asymmetric direction for the construction of molecules related to (IV).

An important step in the synthetic route is the hydrolysis of hydroxy boronic ester (V) to the chiral diol (VI) and 1,2-oxaborolane (VII). This step enables efficient recovery of the valuable chiral diol (VI) at an early stage of the synthesis, and allows easy purification of the 1,2-oxaborolane intermediate. The hydrolysis is effected by aqueous base in the presence of a separate organic phase under conditions where the anionic hydroxylated 1,2-oxaborolane (XVI) is partitioned into the aqueous phase as a salt, and the chiral diol (VI) is separated into the organic phase. Acidification of the separated aqueous phase releases the 1,2-oxaborolane (VII), which on concentration is isolated as the anhydride (XVII).

Intermediate (XVII) contains a masked hydroxyl group, which is unmasked by esterification of the boron functionality with a suitable diol (VIII, n=2–6, R=alkyl or cycloalkyl of 1 to 10 carbon atoms) to form hydroxy boronic ester (IX). An equilibrium mixture of (IX) with (VIII) and (VII) or (XVII) and related derivatives is obtained, but oxidation of this mixture by the use of a coventional reagent for oxidizing secondary alcohols to ketones, such as pyridinium dichromate, leads to the keto boronic ester (X). It is preferred to choose a diol (VIII) that is not easily oxidized, for example, pinacol [(VIII), R=$CH_3$, n=2]. The intermediate (V) (R²=cyclohexyl) is functionally equivalent to (IX) and has been oxidized successfully to (X) (R²=H,cyclohexyl), but there can be loss of chiral diol (VI) due to oxidation in a side reaction, thereby lowering the yield of (X). Inasmuch as 1,3-diols (VIII), n=3 are also known to form stable cyclic boronic esters, a 1,3-diol may be used in place of the 1,2-diol.

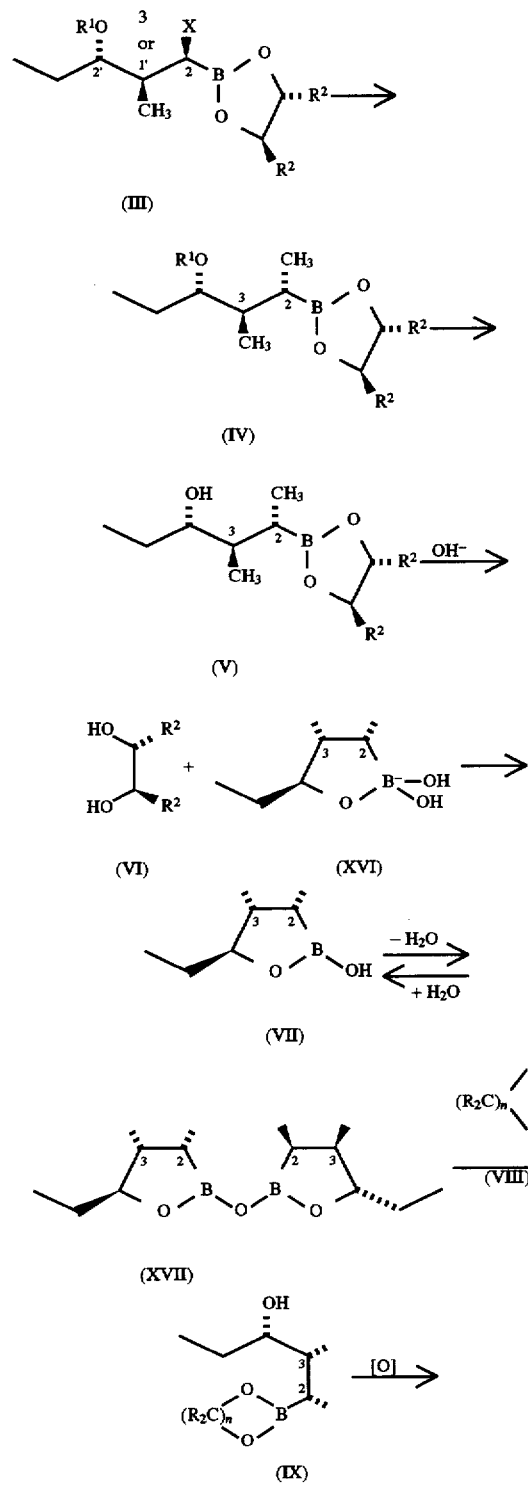

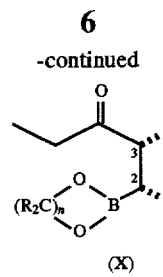

In the second stage of the synthesis of stegobiol, the keto boronic ester (X) is converted to a suitable enolate for aldol condensation with the aldehyde (XIII). A particular example of aldehyde (XIII) is (2S,3S)-3-benzyloxy-2-methylpentanal, R¹benzyl, and a particular example of keto boronic ester (X) is (1'S,2'R)-4,4,5,5-tetramethyl-2(1',2'-dimethyl-3'-oxopentyl)-1,3,2-dioxaborolane. A lithium enolate is useful (Matteson & Man (1993) supra), and dialkylboron enolates are preferred. The reagent (XI) used for making the enolate may be a dialkylboron halide (R³=alkyl, X=Cl, Br, or I) or triflate (X=CF₃SO₂O). Examples of R³ groups in (XI) include n-butyl, n-hexyl, and cyclohexyl, and a particularly preferred example is BR³₂=9-borabicyclononyl. A preferred procedure utilizes (XI)=9-bromo-9-borabicyclononane. The enolate (XII) is illustrated as the (Z)-isomer, but the (E)-isomer is also presumably present, and either may lead to (XIV).

Final conversion of intermediate (XIV) to O-protected stegobiol (XV) requires oxidation of the hydroxyl function to a ketone, oxidative deboronation with hydrogen peroxide to replace the carbon-boron bond with a carbon-oxygen bond, and acid catalyzed ring closure.

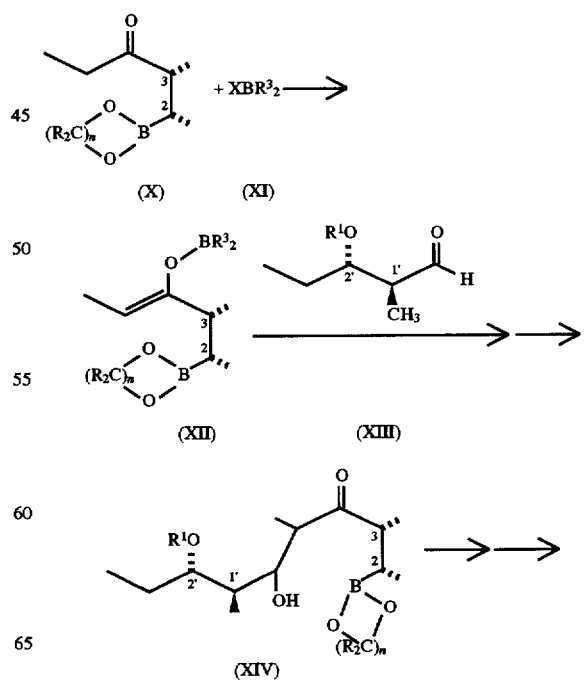

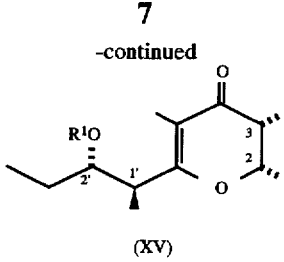

(XV)

The successful oxidations of hydroxy substituted boronic esters to keto boronic esters by anhydrous pyridinium chromate is an additional novel and unexpected feature of this synthetic route, as it is well established that aqueous chromate readily oxidizes boronic acids (Ware & Traylor (1963) J. Am. Chem. Soc. 85:3026) or trialkylboranes (Brown & Garg (1961) J. Am. Chem. Soc. 83:2951). The more expensive perruthenate catalyzed oxidation with an amine oxide has no precedent with regard to boronic esters. The oxidation by Swern's method was established earlier (Matteson et al. (1990) J. Am. Chem. Soc. 112:3964–3969), but has the disadvantage that dimethyl sulfoxide and dimethyl sulfide, a starting material and a product, respectively, in the Swern process, may cause problems in subsequent steps by inhibiting hydrogenations and crystallizations.

The availability of a pure form of active stegobinone allows for economical uses of small amounts of material since earlier synthesis and isolation resulted in impure mixtures. Important uses of stegobinone are as a monitoring agent and as an insect control agent. As a monitoring agent, it is used as an attractant, for example, in a trap. The number and frequency of collection of beetles indicate whether they are present and can be correlated to the size of the local beetle population. This information can be used to determine the time of beetle emergence, and therefore allows accurate timing for pesticide application.

As a control agent, stegobinone can be used in a trap to lure large numbers of beetles, with or without the use of insecticides in the trap. It is also possible that stegobinone, in large enough doses, can disrupt normal mating, thereby eliminating egg-laying.

The following examples are meant to illustrate, but not to limit, the invention.

EXAMPLES

Example 1

(4R,SR,1'S,2'R,3'S)-2-[1'-2-Dimethyl-3'-(phenylmethoxy) pentyl]-4,5-dicyclohexyl-1,3,2-dioxaborolane (IV)

A solution of crude (4R,5R, 1'S,2'S)-4,5-dicyclohexyl-2-[1'-methyl-2'(phenylmethoxy)butyl]-1,3,2-dioxaborolane (Matteson & Man (1993) supra) (47 g) and dichloromethane (34 g, 400 mmol) in tetrahydrofuran (THF) (200 ml) was treated with lithium diisopropylamide (LDA) (80 ml, 2M, 160 mmol) added dropwise at −40° C. After 10 min, zinc chloride (47 g, 345 mmol), which had been fused before use, was added to the solution. The resulting solution of (4R,5R, 1'S,2'S,3'S)2-[1'-chloro-2'-methyl-3'-(phenylmethoxy) pentyl]4,5-dicyclo-hexyl-1,3,2-dioxaborolane (III) was allowed to warm to room temperature and kept for 18 h. The solution was cooled to 0° C. and methylmagnesium chloride (136 ml, 2.5M, 340 mmol) was added dropwise. The solution was allowed to warm to room temperature and kept for 36 h. Aqueous ammonium chloride (20 ml) was added to the mixture. Some gas (methane) was liberated. The solvent was removed by vacuum distillation. To the mixture was added pentane (800 ml) and saturated aqueous ammonium chloride (400 ml). The organic solution was washed with ammonium chloride solution (300 ml) followed by water (3× 300 ml) and dried over magnesium sulfate. Concentration in a rotary evaporator gave an oil (52 g) containing (4R,5R,1'S,2'R,3'S) -4,5-dicyclohexyl-2-[1',2'-dimethyl-3'-(phenylmethoxy) pentyl)-1,3,2-dioxaborolane (IV) and (4R,5R)-4,5-dicyclohexyl-2-methyl-1,3,2-dioxaborolane. The crude (IV) was used in the next step without further purification.

Example 2

(4R,5R, 1'S,2'R,3'S)-2-(1',2'-Dimethyl-3'-hydroxypentyl)-4,5-dicyclohexyl-1,3,2-dioxa-borolane (V)

A solution of crude (4R,5R, 1'S,2'R,3'S)-4,5-dicyclohexyl-2-[1',2'-dimethyl-3'(phenylmethoxy) pentyl)-1,3,2-dioxaborolane (IV) (52 g) in ethyl acetate (400 ml) was stirred with palladium on charcoal catalyst (8 g, 10%) under 1 atm of hydrogen until thin layer chromatography or gas chromatography showed no (IV) remaining. The mixture was filtered through a pad of Celite. Concentration in a rotary evaporator gave a mixture of (4R,5R)-4,5-dicyclohexyl-2-(1'-methylethyl)-1,3,2-dioxaborolane, (4R,5R)]-4,5 dicyclohexyl-2-methyl-1,3,2-dioxaborolane, and (4R,5R, 1'S,2'R,3'S)-2-(1',2'-dimethyl-3'-hydroxypentyl)-4,5-dicyclohexyl-1,3,2-dioxaborolane (V) (39.8 g), which was used in the next step without further purification.

Example 3

(3S,4R,5S,3'S,4'R,5'S]-2,2'-Oxybis(3,4-dimethyl-5- ethyl-1, 2-oxaborolane) (XVII)

A solution of crude (4R,5R,1'S,2'R,3'S)-2-(1',2'-dimethyl-3'-hydroxypentyl)-4,5-dicyclohexyl-1,3,2-dioxaborolane (V) (39.8 g) in diethyl ether (400 ml) was stirred with sodium hydroxide (1M, 400 ml) at room temperature for 8 h. At this point the ratio of free (R,R)-1,2-dicyclohexyl-1, 2-ethanediol to unhydrolyzed (4R,5R, 1'S,2'R,3'S)-2-(1',2'-dimethyl-3'-hydroxypentyl)-4,5-dicyclohexyl-1,3,2-dioxaborolane (V) in the ether phase was 4:1 as determined by GC and proton NMR analysis. The 1,2-dicyclohexylethanediol (VI, R²=cyclohexyl) was removed by separating the organic layer and evaporating diethyl ether. The oily residue was redissolved in diethyl ether (300 ml) and returned to the sodium hydroxide aqueous layer for another 8 h until GC or NMR showed no (V) left. The sodium hydroxide aqueous layer was acidified with hydrochloric acid to pH 2~3. The solution was extracted with ethyl acetate (2×400 ml) and dried over magnesium sulfate. Concentration in a rotary evaporator gave pure (3S,4R,5S, 3'S,4'R,5'S)-2,2'-oxybis(3,4-dimethyl-5-ethyl-1,2-oxaborolane) (XVII) (8.5 g) [47% overall yield from (4R, SR)-4,5-dicyclohexyl-2-ethyl-1,3,2-dioxaborolane]; $^1$H-NMR(CDCl$_3$) δ 0.91 (d,J=7.9 Hz, 3, CH$_3$), 0.93 (d,J=7.0 Hz, 3, CH$_3$), 0.98 (t, J=7.3 Hz, 3, CH$_3$CH$_2$), 1.40 (m, 2, CH$_2$CH$_3$), 1.61 (m, 1, CHCH$_3$), 1.98 (m, 1, CHCH$_3$), 3.76 (dt, J=4.1, 7.3 Hz, 1, CH O); 75-MHz $_{13}$C-NMR (CDCl$_3$) δ 8.18, 10.25, 13.89, 20.55 (br), 27.88, 40.43, 86.78; HRMS calculated for C$_{14}$H$_{28}$B$_2$O$_3$(M+) 266.2225, found 266.2196.

Example 4

(1'S,2'R)-4,4,5,5-Tetramethyl-2-(1',2'-dimethyl-3'-oxopentyl)-1,3,2-dioxaborolane (X)

A solution of (3S,4R,5S,3'S,4'R,5'S)-2,2'-oxybis(3,4-dimethyl-5-ethyl-1,2-oxaborolane) (XVII) (8.5 g, 31.9 mmole) and pinacol (VIII, R=CH$_3$, n=2)(11.3 g, 95.8 mmole) in diethyl ether (150 ml) was stirred at room temperature for 1 h. Concentration in a rotary evaporator gave a mixture of four different compounds, presumably including (IX). One of the constituents had the composition of (XVII) plus pinacol [HRMS calculated for $C_{20}H_{40}O_4B_2$ (M+) 366.3113, found 366.3088]. A solution of the foregoing mixture, pyridinium dichromate (108 g), and molecular sieves (40 g) in dichloromethane (300 ml) was stirred at room temperature for 3 h. Celite (30 g) and silica gel (30 g) were added to the mixture and stirred for 30 min. The mixture was filtered though a short pad of Florisil. The solid was washed with ethyl acetate (2×200 ml). Concentration in a rotary evaporator and purification by redissolving in pentane (300 ml) and filtering was followed by washing with water (2×200 ml). The pentane solution was dried over magnesium sulfate. Concentration in a rotary evaporator gave (1'S,2'R)-4,4,5,5-tetramethyl-2-(1',2'-dimethyl-3'-oxopentyl)-1,3,2-dioxaborolane (X, n=2, R=CH$_3$) as an oil (13 g, 54 mmole), 39.7% overall yield from (4R,5R)-4,5-dicyclohexyl-2-ethyl-1,3,2-dioxaborolane; $^1$H-NMR (CDCl$_3$) δ 0.91 (d,J=7.9 Hz, 3, CH$_3$), 1.03 (t,J=7.2 Hz, 3, CH$_3$CH$_2$), 1.11 (d,J=7.0 Hz, 3, CH$_3$), 1.24 (s, 12, CH$_3$), 2.3–2.5 (m, 3, CH2CH3, CHCH3), 2.62 (dq, J=7.1, 7.2 Hz, 1, CHCH3);75-MHz 13C-NMR(CDCl3) δ 7.69, 13.07, 16.01, 24.64, 24.73, 34.35, 48.63, 82.97, 215.53; HRMS calculated for $C_{13}H_{25}BO_3$ (M+) 240.1897, found 240.1874. Anal. Calculated for $C_{13}H_{25}BO_3$: C, 65.02; H 10.49 B, 4.50. Found: C, 64:83; H, 10.20, B, 4.16.

Example 5

(4R,5R,1'S,2'R)-2-(3'-Oxo-1',2'-dimethylpentyl)-4,5-dicyclohexyl-1,3,2-dioxaborolane [X, n =2, R$_2$C= (cyclohexyl)HC].

(a) Via oxidation with tetrapropylammonium perruthenate and N-methylmorpholine N-oxide. A mixture of crude (4R, 5R,1'S,2'R,3'S)-2- (3'-hydroxy- 1',2'dimethylpentyl)-4,5-dicyclohexyl-1,3,2-dioxaborolane (V, R$^2$=cyclohexyl) (0.4 g), tetrapropylammonium perruthenate (TPAP) (29 mg), N-methylmorpholine N-oxide (0.221 g, 1.9 mmol) and molecular sieves (2 g) in 10 ml of dichloromethane was stirred at room temperature for 1 h (Griffith et al. (1987) J. Chem. Soc., Chem. Commun. VOL?:1625). The product [X, n=2, R$_2$C=(cyclohexyl)HC] was filtered through a pad of Celite, then purified by flash column chromatography (silica, dichloromethane) to give an oil (0.25 g); 300-MHz $^1$H-NMR (CDCl3) δ 0.80–1.80 (m, 32, including C$_6$H$_{11}$, 0.93 (d,J=7.5 Hz, BCHCH$_3$), 1.03 (t, J=7.3 HZ, C$_2$CH$_3$), 1.11 (d, J=7.1 HZ, CHCH$_3$)), 2.32–2.64 (m, 3H, OCCH, OCCH$_2$), 3.80–3.86 (m, 2H, BOCH); 75-MHz $^{13}$C-NMR (CDCl$_3$) δ 7.70, 13.88, 15.92, 25.87, 25.98, 26.45, 27.52, 28.44, 34.28, 42.97, 48.90, 83.40, 215.65. HRMS calculated for $C_{21}H_{37}BO_3$ (M+) 348.2836, found 348.2817. Anal.?? calculated for $C_{21}H_{37}BO_3$: C, 72.41; H, 10.71; B, 3.10. Found: C, 72.55; H, 11.07; B, 3.19.

(b) Via oxidation with pyridinium dichromate. A mixture of crude (4R,5R,1'S,2'R,3'S)-2-(3'-hydroxy-1',2'-dimethylpentyl)-4,5-dicyclohexyl-1,3,2-dioxaborolane (V, R$^2$=cyclohexyl) (0.7 g), pyridinium dichromate (6 g), and molecular sieves (3 g) in dichloromethane (20 ml) was stirred at room temperature for 3 h. Celite (2 g) and silica gel (2 g) were added to the mixture and stirred for 30 min. The mixture was filtered though a short pad of Florisil. The solid was washed with ethyl acetate (2×50 ml). Concentration in a rotary evaporator and purification by flash column chromatography (silica, dichloromethane/pentane 5:1) gave as an oil (0.35 g) [38.5% overall yield from (4R,5R)-4,5-dicyclohexyl-ethyl-1,3,2-dioxaborolane].

(c) Via Swern's method of oxidation. To a solution of oxalyl chloride (0.39 g, 3.1 mmol) in dichloromethane (7 ml) was added dimethyl sulfoxide (0.525 g, 6.7 mmol) dropwise at 60° C. After 10 min, the crude (4R,5R, 1'S,2'R, 3'S)-2-(3'-hydroxy-1',2'-dimethylpentyl)-4,5-dicyclohexyl-1,3,2-dioxaborolane (V, R$^2$=cyclohexyl) (0.7 g) in 7 ml of dichloromethane was added at –60° C. The cloudy mixture was stirred for 20 min at –60° C. To the solution was added triethylamine (2 ml, 14 mmol). After 5 min, the cold bath was removed and the solution was allowed to warm to room temperature. Water (10 ml) was added and the solution was stirred for 10 min. The organic layer was separated from the aqueous solution. The aqueous layer was extracted with dichloromethane (2×30 ml). The combined organic layer was washed with ammonium chloride and water (20 ml each), and dried over magnesium sulfate. Distillation of solvent and purification by flash column chromatography (silica, dichloromethane/pentane 5:1) gave X, n=2, R$_2$C= (cyclohexyl)HC] as an oil (0.35 g), 38.5% overall yield from (4R,5R)-dicyclohexyl-2-ethyl-1,3,2-dioxaborolane. 1,2-Dicyclohexyl-2-hydroxyethanone and unreacted alcohol were detected in the NMR spectrum of the crude product and separated by column chromatography.

Example 6

O-Benzylstegobiol (XV)

(1'S,2'R)-4,4,5,5-Tetramethyl-2-(1',2'-dimethyl-3'-oxopentyl)-1,3,2dioxaborolane [X, n=2, R$_2$C=(CH$_3$)$_2$C] (2.71 g, 11.3 mmol) was added dropwise to a stirred solution of (bromo)(dihexyl) borane (3.53 g, 13.5 mmol) and triethylamine (1.36 g,13.5 mmol) in diethyl ether (15 ml) kept at 0° C. under argon. After stirring for 6 h, the solution was cooled to –78° C. for 15 min. A solution of (2S,3S)-3-benzyloxy-2-methylpentanal (XIII, R$^1$=benzyl) (2.32 g, 11.3 mmol) in 5 ml of diethyl ether was added via syringe at –78° C. The solution was stirred for 12 hr. To the solution was added ether (30 ml) and aqueous ammonium chloride (20 ml). The aqueous layer was extracted with ether (3×20 ml). The combined organic layer was washed with brine (100 ml) and dried over magnesium sulfate. Concentration in a rotary evaporator gave a product (6.86 g) containing keto boronic ester (X), aldehyde (XIII), and aldol condensation product (1'S,2'R,4'R or S,5'R or S,6'R,7'S)-2-(7'-benzyloxy-5'-hydroxy-3'-oxo-1',2',4',6 '-tetramethyl)nonyl-4,4,5,5-tetramethyl-1,3,2-dioxaborolane [XIV, n=2, R$_2$C=(CH$_3$)$_2$C]. The solution of the crude mixture in dichloromethane (50 ml) was stirred with pyridinium dichromate (37.6 g, 100 mmol) and molecular sieves (4 Å, 8 g) at room temperature for 12 h. Celite was added to the mixture and stirred for 30 min. The mixture was filtered though a short pad of Florisil. The solid was washed with ethyl acetate (100 ml). Concentration in a rotary evaporator gave a mixture of ketoboronate (X), aldehyde (XIII), and (1'S,2'R,4'R or S,6'R,7'S)-2-(7'-benzyloxy-3',5'-bisoxo-1',2',4',6'-tetramethyl)nonyl-4,4,5,5-tetramethyl-1,3,2-dioxaborolane (not illustrated) (6.8 g). To a solution of the above mixture in 100 ml of THF and 50 ml of phosphate buffer (pH 8) was added hydrogen peroxide (6 ml, 30%) at 0° C. After 0.5 h, the cold bath was removed. After 3 h at room temperature, the solution was treated with sodium iodide and sodium thiosulfate. The THF solution was separated from the aqueous solution. The aqueous layer was extracted with ether (2×100 ml). The combined organic layer was washed with sodium thiosulfate (10%) solution (300 ml) and dried over magnesium sulfate. Concentration in a rotary evaporator gave a mixture of deboronated product (4.92 g). A solution of above mixture in CDCl$_3$ (30 ml) was stirred with trifluoroacetic acid (10 ml) at room temperature. The reaction was followed by $^1$H-NMR analysis. After 50 min, the reaction was completed. Ether (200 ml) was added to the solution. The solution was washed with sodium bicarbonate (sat., 100 ml) and dried over magnesium sulfate. Concentration in a rotary evaporator and separation of product by flash column chromatography (silica, 20% ether/hexanes) gave O-benzylstegobiol (XV) (1.1 g, 3.48 mmol, 31.6% from (X)).

Example 7

O-Benzylstegobiol (XV) from (4R,5R,1'S,2'R)-4,5-dicyclohexyl-2-(1',2'-dimethyl-3'oxopentyl)-1,3,2-dioxaborolane [X, n=2, $R_2C$=(cyclohexyl)HC]

To a solution of tetramethylpiperidine (0.29 g, 2.1 mmol) in THF (5 ml) was added n-butyllithium (1.23 ml, 1.4 M, 1.72 mmol) dropwise at 0° C. After stirring at 0° C. for 15 min, the solution was cooled to −78° C. for 15 min. A solution of (4R,5R, 1'S,2'R)-4,5-dicyclohexyl-2-(1', 2'-dimethyl-3'-oxopentyl)-1,3,2-dioxaborolane [X, n=2, $R_2C$=(cyclohexyl)HC] (0.6 g, 1.72 mmol) in 2 ml of THF was added via syringe at −78 ° C. After 30 min, a solution of (2S,3S)-3-benzyloxy-2-methylpentanal (XIII, $R^1$=benzyl) (0.35 g, 1.7 mmol) in 1 ml of THF was added via syringe at −78° C. After 45 min, aqueous ammonium chloride (1 ml) was added. The cold bath was removed and the solution was allowed to warm to room temperature. To the solution was added ether (30 ml) and aqueous ammonium chloride (20 ml). The aqueous layer was extracted with ether (3×20 ml). The combined organic layer was washed with brine (50 ml) and dried over magnesium sulfate. Concentration in a rotary evaporator gave a product (1 g) containing ketoboronate [X, n=2, $R_2C$=(cyclohexyl)HC], aldehyde, and aldol condensation product, (4R,5R, 1'S,2'R, 4'R or S,5'R or 6'R,7'S)-2-(7'-benzyloxy-5'-hydroxy-3'-oxo-1', 2',4',6'-tetramethyl)nonyl-4,5-dicyclohexyl-1,3,2-dioxaborolane [XIV, $R^1$=benzyl, n=2, $R_2C$=(cyclohexyl)HC]. The solution of the crude mixture in dichloromethane (50 ml) was stirred with pyridinium dichromate (5.4 g, 10 mmol) and molecular sieves (4 A,3 g) at room temperature for 3 h. Celite was added to the mixture and stirred for 30 min. The mixture was filtered though a short pad of Florisil. The solid was washed with ethyl acetate (50 ml). Concentration in a rotary evaporator gave a mixture of ketoboronate [X, n=2, $R^2C$=(cyclohexyl)HC], aldehyde (XIII, $R^1$=benzyl), and the diketone (4R,5R, 1'S,2'R,4'R or S,6'R, 7'S)-2-(7'-benzyloxy-3',5'-bisoxo-1',2',4',6'-tetramethyl)nonyl-4,5-dicyclohexyl-1,3,2-dioxaborolane (not illustrated) (0.62 g). To a solution of the above mixture in 10 ml of THF and 10 ml of phosphate buffer (pH 8) was added hydrogen peroxide (0.5 ml, 30%) at 0° C. After 0.5 h, the cold bath was removed. After 3 h at room temperature, the solution was treated with sodium iodide and sodium thiosulfate. The THF solution was separated from the aqueous solution. The aqueous layer was extracted with ether (2×50 ml). The combined organic layer was washed with sodium thiosulfate (10%) solution (20 ml) and dried over magnesium sulfate. Concentration in a rotary evaporator gave a mixture of aldehyde (VIa), (4R,5R,1'S,2'R)-4,5-dicyclohexyl-2(1',2'-dimethyl-3'-oxopentyl)-1,3,2-dioxaborolane and O-benzylstegobiol (0.6 g). A solution of above mixture in $CDCl_3$ (1 ml) was stirred with trifluoroacetic acid (12 drops) at room temperature. The reaction was followed by $^1$H-NMR. After 15 min, the reaction was completed. Ether (20 ml) was added to the solution. The solution was washed with sodium bicarbonate (sat., 10 ml) and dried over magnesium sulfate. The NMR spectrum of crude product showed impurity peaks characteristic of aldehyde (XIII, $R^1$=benzyl), diastereomer of (XIII), and (4R, 5R)-4,5-dicyclohexyl-2-hydroxy-1,3,2-dioxaborolane. Concentration in a rotary evaporator and separation of product by flash column chromatography (silica, 20% ether/hexanes) gave O-benzylstegobiol (XV) (0.17 g, 0.53 mmol, 31% from (X)).

What is claimed is:

1. A method for reacting (1'S,2'R)-2-(1',2'-dimethyl-3'-oxopentyl) -1,3,2-dioxaborin having structure:

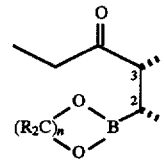

wherein n=2, R=H, alkyl or cycloalkyl of up to 10 carbon atoms with a 3-O-protected (2S,2S)-3-hydroxy-2-methylpentanal having structure:

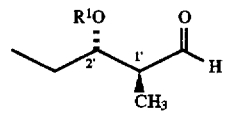

wherein $R^1$ is a hydroxy-protecting group to form an 8-O-protected (2S,3R, 5R or S,6R or S,7R,8S) -2-(1,3,2-dioxaborol-2-yl)-6-hydroxy-8-hydroxy 3,5,7-trimethyl-decanone having structure:

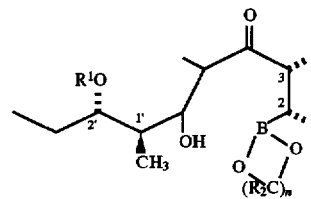

comprising the step of reacting a dialkylboron halide or triflate, $XBR^3_2$ wherein $R^3$ is alkyl or cyclohexyl or $BR^3_2$ represents 9-borabicyclononyl, X is halogen or triflate, with said dioxaborin in the presence of a base, prior to reaction with said pentanal.

2. The method of claim 1, wherein said base comprises trialkylamine.

3. The method of claim 1, wherein said dioxaborin is a (1'S,2'R)-2-(1',2'-dimethyl-3'-oxopentyl)-1,3,2-dioxaborolane and the product is a (2S,3R,5R or S,6R or S,7R,8S)-2-(1,3,2-dioxaborol-2-yl)-6-hydroxy-8-organyloxy-3,5,7-trimethyl-decanone.

4. The method of claim 1 wherein said dioxaborin is (1'S,2'R)-4,4,5,5-tetramethyl-2-(1', 2'-dimethyl-3'-oxopentyl)-1,3,2-dioxaborolane.

5. The method of claim 1, wherein said pentanal is (2S,3S)-3-benzyloxy-2-methylpentanal.

6. The method of claim 1 wherein said dialkylboryl group $BR^3_2$ is dibutylboryl and the group X is Cl, Br, I, or $F_3CSO_3$.

7. The method of claim 1 wherein said dialkylboron halide is selected from the group consisting of dihexylboryl chloride, bromide, and iodide and said dialkylboron triflate is dihexylboryl triflate.

8. The method of claim 1 wherein said dialkylboron halide is selected from the group consisting of dicyclohexylboryl chloride, bromide and iodide and said dialkylboron triflate is dicyclohexylboryl triflate.

9. The method of claim 1 wherein said dialkylboron halide is selected from the group consisting of 9-borabicyclononyl chloride, bromide and iodide and said dialkylboron triflate is 9-borabicyclononyl triflate.

10. The method of claim 1 wherein said dioxaborin is reacted with dialkylboron triflate.

11. The method of claim 1 wherein said dioxaborin is reacted with dialkylboron chloride.

12. The method of claim 1 wherein said dioxaborin is reacted with dialkylboron bromide.

13. The method of claim 1 wherein said dioxaborin is (1'S,2'R)-4,4,5,5-tetramethyl-2-(1', 2'-dimethyl-3'-oxopentyl)-1,3,2-dioxaborolane, said pentanal is (2S,3S)-3-benzyloxy-2 methylpentanal and said dialkylboron halide is 9-bromo-9- borabicyclo[3.3.1]nonane.

14. A method according to any of claims 1–13 wherein said formed decanone contains all the chirality and functionality of stegobiol in protected form.

* * * * *